United States Patent [19]
Cheng et al.

[11] Patent Number: 5,618,964
[45] Date of Patent: Apr. 8, 1997

[54] PRODRUG ESTERS OF PHOSPHONOSULFONATE SQUALENE SYNTHETASE INHIBITORS AND METHOD

[75] Inventors: Peter T. W. Cheng; Michael A. Poss, both of Lawrenceville, N.J.

[73] Assignee: Bristol-Myers Squibb Company, Princeton, N.J.

[21] Appl. No.: 487,383

[22] Filed: Jun. 7, 1995

[51] Int. Cl.$^6$ .................................................. C07F 9/40
[52] U.S. Cl. ............................................................ 558/180
[58] Field of Search ............................................. 558/180

[56] References Cited

U.S. PATENT DOCUMENTS 5,332,728  7/1994  Biller ........................ 514/107

FOREIGN PATENT DOCUMENTS

0595635A1  5/1994  European Pat. Off. .
9324495  12/1993  WIPO .

*Primary Examiner*—Johann Richter
*Assistant Examiner*—Laura R. Cross
*Attorney, Agent, or Firm*—Burton Rodney

[57] ABSTRACT

New prodrug esters of salt forms of the phosphonosulfonate squalene synthetase inhibitor having the structure

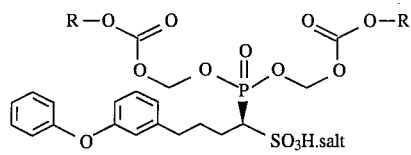

are provided wherein R is alkyl, arylalkyl, aryl or acylthioalkyl. These prodrug esters inhibit cholesterol biosynthesis and therefore are used in lowering serum cholesterol and in treating atherosclerosis.

12 Claims, No Drawings

PRODRUG ESTERS OF PHOSPHONOSULFONATE SQUALENE SYNTHETASE INHIBITORS AND METHOD

FIELD OF THE INVENTION

The present invention relates to prodrug esters of salts of the phosphonosulfonate squalene synthetase inhibitor 3-phenoxy-α-phosphonobenzenebutanesulfonic acid, and to their use in inhibiting de novo cholesterol biosynthesis, in lowering serum cholesterol and in treating atherosclerosis.

BACKGROUND OF THE INVENTION

European Patent Application No. 0595635A1 discloses α-phosphonosulfonate compounds which inhibit cholesterol biosynthesis, and thus are useful as hypocholesterolemic and antiatherosclerotic agents and have the following structure

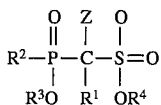

wherein $R^2$ is $OR^5$ or $R^{5a}$, $R^3$ and $R^5$ are the same or different and are H, alkyl, arylalkyl, aryl, cycloalkyl, a metal ion or other pharmaceutically acceptable cation as defined below, or a prodrug ester;

$R^{5a}$ is H, alkyl, arylalkyl or aryl;

$R^4$ is H, alkyl, cycloalkyl, aryl, arylalkyl, metal ion or other pharmaceutically acceptable cation as defined below, or a prodrug ester;

z is H, halogen, lower alkyl or lower alkenyl;

$R^1$ is a lipophilic group containing at least 7 carbons and is alkyl containing from 7 to 25 carbons in the chain; alkenyl containing from 7 to 25 carbons in the chain and from 1 to 6 double bonds; alkynyl containing from 7 to 25 carbons in the chain and from 1 to 6 triple bonds; mixed alkenyl-alkynyl containing 1 to 5 double bonds and 1 to 5 triple bonds; cycloalkyl; cycloheteroalkyl linked through a carbon on the ring or a heteroatom; aryl; heteroaryl; heteroarylalkyl; cycloalkylalkyl; cycloheteroalkylalkyl; or a group of the structure

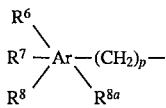

wherein Ar is aryl (such as phenyl or naphthyl), heteroaryl (5 or 6 membered) and may include one to three additional rings fused to Ar (such as aryl, cycloalkyl, heteroaryl or cycloheteroalkyl) and wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, preferably from 3 to 25 carbons, alkoxy containing 1 to 40 carbons, preferably from 3 to 25 carbons, alkenyl containing 2 to 40 carbons, preferably from 3 to 25 carbons, alkenyloxy containing 2 to 40 carbons, preferably from 3 to 25 carbons, alkynyl containing 2 to 40 carbons, preferably from 3 to 25 carbons, alkynyloxy containing 2 to 40 carbons, preferably from 3 to 25 carbons, cycloheteroalkyl, cycloheteroalkylalkyl, heteroaryl, cycloalkyl, cycloalkylalkyl, Ar-alkyl, (such as arylalkyl), ArO (such as aryloxy), Ar-amino (such as arylamino), hydroxy, halogen, nitro, Ar (such as aryl), amino, substituted amino wherein the amino includes 1 or 2 substituents (which are alkyl, alkenyl, aryl or any of the Ar groups mentioned above), thiol, alkylthio, Ar-thio (such as arylthio), alkyl-sulfinyl, Ar-sulfinyl (such as arylsulfinyl), alkylsulfonyl, Ar-sulfonyl (such as arylsulfonyl), carboxy, cyano, alkoxycarbonyl, aminocarbonyl, alkylcarbonyloxy, Ar-carbonyloxy (such as arylcarbonyloxy), Ar-carbonylamino (such as arylcarbonylamino) or alkylcarbonylamino, as well as any of the Ar groups as defined above, and preferably wherein the total number of carbons in the substituted Ar—$(CH_2)_p$— group exceeds 10 carbons; including pharmaceutically acceptable salts thereof such as alkali metal salts such as lithium, sodium or potassium, alkaline earth metal salts such as calcium or magnesium, as well as zinc or aluminum and other FDA approved cations such as ammonium, choline, diethanolamine, ethylenediamine, and salts of naturally occurring amino acids such as arginine, lysine, alanine and the like.

The $(CH_2)_p$ group may contain 1, 2, 3 or more alkyl, alkoxy, alkenyl, alkynyl, hydroxy and/or halogen substituents as well as any of the substituents defined for $R^6$.

The term "prodrug esters" as employed in the European Patent Application No. 0595635A1 includes prodrug esters which are known in the art for both phosphorus and carboxylic acids. Examples include the following groups: (1-alkanoyloxy)alkyl such as,

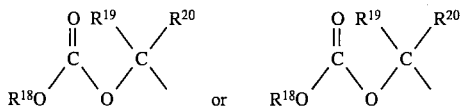

wherein $R^{18}$, $R^{19}$ and $R^{20}$ are H, alkyl, aryl or arylalkyl; however $R^{18}O$ cannot be HO. Examples of such prodrug esters include

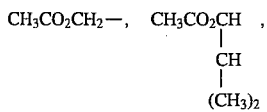

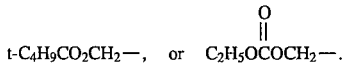

European Patent Application No. 0595635A1 also discloses the preparation of the squalene synthetase inhibitor 3-phenoxy-α-phosphonobenzenebutanesulfonic acid tripotassium salt, including enantiomers thereof, which has the structure

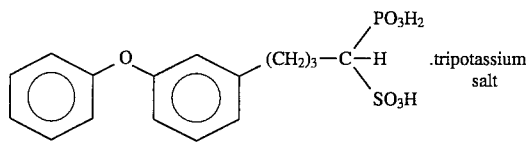

DESCRIPTION OF THE INVENTION

In accordance with the present invention, prodrug esters of phosphonosulfonate salts are provided which have the structure I

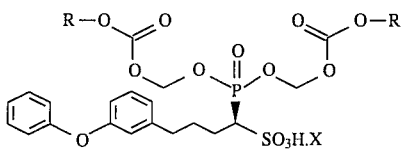   I wherein R is alkyl preferably containing at least 3 carbons, arylalkyl, aryl or acylthioalkyl, and X is a salt as described hereinafter, including all stereoisomers thereof.

Preferred R groups include t-$C_4H_9$, $C_6H_5$—, t-$C_4H_9CH_2$—, t-butyl-$CH_2$,

$C_6H_5CH_2$— or

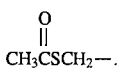

Most preferred is where R is t-butyl.

The moiety X includes pharmaceutically acceptable salts, such as alkali metal salts such as lithium, sodium or potassium, alkaline earth metal salts such as calcium or magnesium, as well as zinc or aluminum and other FDA approved cations such as ammonium, choline, diethanolamine, and ethylenediamine, and salts of naturally occurring amino acids such as arginine, lysine, alanine and the like, and alkylamine salts, such as t-butylamine salt, t-octylamine salt and dehydroabietylamine salt.

It has been found that the above prodrug esters are water-soluble, non-hygroscopic, exhibit a high degree of crystallinity, have good shelf life and provide good oral bioavailability of the squalene synthetase inhibitor.

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or $CF_3$, alkoxy, aryl, arylalkyl, alkenyl, cycloalkyl, amino, hydroxy, alkylamido, alkanoylamino, arylcarbonylamino, nitro, cyano, thiol and/or alkylthio.

Unless otherwise indicated, the term "aryl" as employed herein refers to monocyclic or bicyclic aromatic groups containing from 6 to 10 carbons in the ring portion, such as phenyl, naphthyl, or phenyl or naphthyl substituted with 1 to 4 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio.

The term "aralkyl", "aryl-alkyl" or "aryl-lower alkyl" as used herein alone or as part of another group refers to alkyl groups as discussed above having an aryl substituent, such as benzyl or phenethyl, or naphthylpropyl.

The term "acyl" as used herein alone or as part of another group refers to alkyl linked to a carbonyl group, arylalkyl linked to a carbonyl group or aryl linked to a carbonyl group.

The term "acylthioalkyl" includes an acyl as described above and preferably has the formula

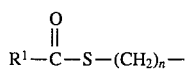

where $R^1$ is alkyl, aryl or arylalkyl,
n is 2 to 6, more preferably 2 or 3, and
wherein any of the carbons in $(CH_2)_n$ may be optionally substituted with 1 or 2 alkyl groups.

Examples of suitable $(CH_2)_n$ groups include

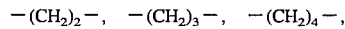

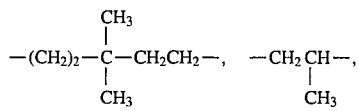

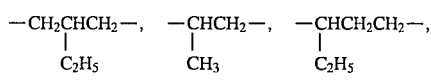

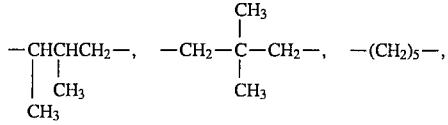

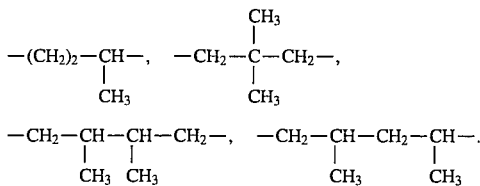

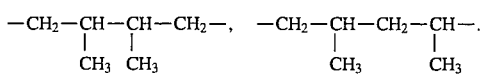

The compounds of formula I of the invention may be prepared as outlined below.

The starting material for preparing compounds of formula I is the phosphonosulfonate triacid, 3-phenoxy-α-phosphonobenzenebutanesulfonic acid, of the structure II

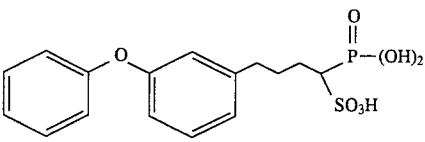   II including all stereoisomers thereof (preferably the (S) enantiomer) (disclosed in European Patent Application 94/0595635A1).

The phosphonosulfonate triacid II is reacted with a carbonate of the structure III

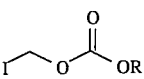   III where R is alkyl, preferably containing at least 2 carbons, aryl, arylalkyl, or acylthioalkyl. The reaction of phosphonosulfonate triacid II and carbonate III is carried out under an inert atmosphere in the presence of acetonitrile or other inert organic solvents such as ethylacetate, toluene or dimethylformamide, and an amine base, such as diisopropylethylamine (Hunigs base), at a temperature within the range from about −20° C. to about 80° C.

The carbonate III will be employed in a molar ratio to phosphonosulfonate II within the range from about 2:1 to about 8:1.

The starting carbonate III may be prepared by reaction of chloromethyl chloroformate IV

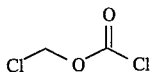

with the alcohol V

in the presence of an inert organic solvent such as methylene chloride, 1,2-dichloroethane or chloroform, and an amine base such as pyridine or collidine, to form the chloride VI.

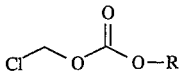

Chloride VI is treated with an alkali metal iodide such as sodium iodide, in the presence of acetonitrile, ethylacetate, dimethylformamide or toluene, at a temperature within the range from about 20° to about 100° C. to form III.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphatedimethylallyl diphosphate isomerase.

The compounds of the invention are useful in treating hyperlipoproteinemia, hyperlipidemia, hypercholesterolemia, hypertriglyceridemia, combined hypercholesterolemia and hypertriglyceridemia, and/or in preventing or inhibiting development of and/or treating atherosclerosis. Thus, the compounds of the invention may be used to treat diseases such as chylomicronemia syndrome, Type I hyperlipoproteinemia, familial combined hyperlipoproteinemia, familial hypertriglyceridemia, mixed hyperlipoproteinemia, familial hypercholesterolemia and Type III hyperlipoproteinemia and/or atherosclerosis.

In addition, the compounds of the invention may increase plasma high density lipoprotein cholesterol levels.

The compounds of the invention may also be useful in inhibiting formation of gallstones, treating hepatitis D (by virtue of protein prenyl-transferase inhibition, Glenn et al, Science, Vol. 256, pp. 1331–1333, May 29, 1992), treating tumors, lowering blood pressure, lowering blood sugar, treating diabetes mellitus, treating inflammation, as a diuretic, as an inotropic agent, as an anti-arthritic (antirheumatic) agent, in treating other diseases of calcium and phosphate metabolism including treatment of bone resorption, Paget's disease, osteoporosis, calcification of joints, implants and metastasis, as antitartar and anti-calculus agents in toothpastes and mouthwashes, treating various stones and calculi, treating sickle cell anemia, treating hypoxia and ischemic tissue, and as an anti-amoebal agent, as well as for use in complexes with technetium-99m and radioiodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranylgeranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys is not farnesylated, in the presence of the protein prenyl transferase inhibitor, it cannot effect interaction of the ras protein with the membrane so that neoplastic transformation of the cell will be prevented. In this manner proteinprenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, ras, nuclear lamins, α or γ subunits of heterotrimeric G-proteins, γ-subunits of retinal transducin, G25K and K-rev p21, and protein families including rho, rap, rac, ral, and rab.

The compounds of the invention may be employed in a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The compounds of the invention may also be employed in combination with an antihyperlipoproteinemic agent, hypocholesterolemic agent, and/or hypotriglyceridemic agent, and/or antiatherosclerotic agent such as one or more HMG CoA reductase inhibitors, for example, pravastatin, lovastatin, simvastatin, velostatin, fluvastatin, rivastatin, compactin, SDZ-63,370 (Sandoz), CI-981 (W-L), HR-780, L-645, 164, CL-274,471, dalvastatin, α-, β-, and γ-tocotrienol, (3R,5S,6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]hydroxy-phosphinyl]-3-hydroxy-butanoic acid, disodium salt, BB-476, (British Biotechnology), dihydrocompactin, [4R-[4α,6β(E)]]-6-[2-[5-(4-fluorophenyl)-3-(1-methylethyl)-1-(2-pyridinyl)-1H-pyrazol-4-yl]ethenyl]tetrahydro-4-hydroxy-2-H-pyran-2-one, and/or 1H-pyrrole-1-heptanoic acid, 2-(4-fluorophenyl)-β,δ-dihydroxy-5-(1-methylethyl)-3-phenyl-4-[(phenylamino)carbonyl]calcium salt[R-(R*,R*)]; one or more fibric acid derivatives such as clofibrate, bezafibrate, Lopid(gemfibrozil) one or more other cholesterol biosynthesis inhibitors, such as NB-598, N-(1-oxododecyl)-4α,10-dimethyl-8-aza-trans-decal-3β-ol, 2,4-undecadienoic acid, 11-[3-(hydroxymethyl)-4-oxo-2-oxetanyl]-3,5,7-trimethyl-, [2R-[2α(2E,4E,7R*),3β]]; one or more bile acid sequestrants, for example, cholestyramine, colestipol, polidexide (DEAE-Sephadex); one or more antioxidants, for example probucol and Vitamin E; and/or one or more other lipid lowering and/or antiatherosclerotic agents, for example nicotinic acid or derivatives thereof, neomycin, p-aminosalicylic acid, probucol, hydroxy-propylmethylcellulose, LS-2904, ethanol, 2-[[1-methyl-2-[3-(trifluoromethyl)phenyl]ethyl]amino]benzoate (ester).

The above compounds to be employed in combination with the squalene synthetase inhibitor of the invention will be used in amounts as indicated in the Physicians' Desk Reference (PDR).

The compounds of the invention may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 mL of physiological saline, to produce an injectible preparation.

The following Examples represent preferred embodiments of the present invention.

EXAMPLE 1

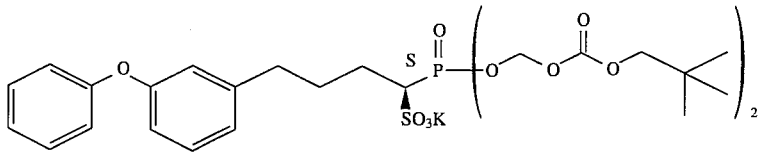

(S)-α-[Bis[[[(2,2-dimethylpropoxy)carbonyl]oxy]-methoxy]phosphinyl]-3-phenoxybenzenebutanesulfonic acid, potassium salt

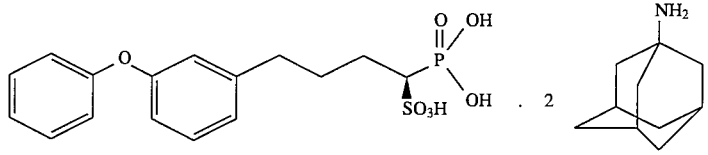 · 2 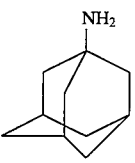

(S)-(−)-3-Phenoxy-α-phosphonobenzenebutanesulfonic acid, 1-adamantanamine (1;2) salt A(1). (1R,2R)-N,N'-Dimethyl-1,2-cyclohexanediamine Preparation of the title compound was carried out as described by Hanessian, S. et. al. J. Amer. Chem. Soc. 1984, 106, 5754–5756, and Alexakis, A. et. al. J. Org. Chem. 1992, 57, 1224–1237, Galsbol, F. et al., Acta Chem. Scand. 1972, 26, 3605 and Onuma, K. et. al., Bull. Chem. Soc. Jpn. 1980, 53, 2012.

$[\alpha spec]_D^{20} = -150°$ CHCl$_3$, (C=1); Literature $[\alpha spec]_D^{20} = -147°$ A(2). [3aR-(3aα,7aβ)]-2-Chlorooctahydro-1,3-dimethyl-1H-1,3,2-benzodiazaphosphole, 2-oxide A solution of 4.72 g (33.20 mmol) of Part A(1) diamine and 12.63 g (125.0 mmol) of triethylamine in 50 mL of toluene at 0° C. was treated with 5.00 g (33.20 mmol) of phosphorus oxychloride dropwise over 15 min. The reaction mixture was stirred for 10 min. at 0° C. and warmed to RT. After 3 h the solids were filtered off and the filtrate concentrated to a slurry. The slurry was purified by flash chromatography (100 g of silica gel) eluting with 15.85 acetone/toluene to provide 6.50 g (88%) of title chloride as a low melting solid.

TLC Silica gel (1:4 acetone/toluene) R$_f$=0.30.

$^1$H NMR (CDCl$_3$, 300 MHz): δ2.85 (td, 1H, J=10.8, 3.0 Hz) 2.67 (d, 3H, J=10.0 Hz) 2.55 (d+m, 4H, J=18.0 Hz) 2.05 (m, 2H) 1.85 (m, 2H) 1.35 (m, 4H) ppm.

$^{13}$C NMR (CDCl$_3$, 75.6 MHz): δ63.5 (d, J=7.0 Hz ) 62.5 (d, J=10.0 Hz ) 28.0 27.5 (d, J=7.0 Hz ) 27.0 (d, J=7.0 Hz) 24.0 23.9 ppm.

$^{31}$P NMR (CDCl$_3$, 121.7 MHz): δ36.6 ppm

A(3). [3aR-(3aα,7aβ)]-Octahydro-1,3-dimethyl-1H-1,3,2-benzodiazaphosphole-2-methanesulfonic acid, ethyl ester, 2-oxide To a rapidly stirred solution of 6.20 g (50.0 mmol) of ethyl methanesulfonate in 150 mL of THF at −73° C. (internal temperature) was added 20 mL (50 mmol) of 2.5M n-butyllithium dropwise over 20 min (The internal temperature was not allowed to rise above −69° C. throughout the addition of n-BuLi). After an additional 30 min., 5.56 g (25.0 mmol) of freshly prepared Part A(2) chloride in 25 mL of THF was added at a rate to keep the solution temperature below −69° C. The reaction mixture was stirred for 0.3 h at −73° C. and for 3 h at −30° C. The reaction mixture was poured into 250 mL of a rapidly stirring mixture of 1:1 saturated aqueous NaHCO$_3$ solution/ethyl acetate. The mixture was partitioned between ethyl acetate and water (3×75 mL). The organic extracts were dried (Na$_2$SO$_4$) and concentrated to an oil. The oil was purified by flash chromatography (200 g silica gel) eluting with methylene chloride (600 mL) followed by 93:7 dichloromethane/isopropanol (1000 mL) to provide 6.60 g (85%) of title compound as a low melting solid.

TLC Silica gel (1:9 2-propanol/dichloromethane) $R_f$=0.58.

IR (KBr) 2947, 2878, 1478, 1451, 1348, 1258, 1236, 1215, 1165, 1123, 1026, 1005, 918 cm$^{-1}$.

Mass Spec (CI–NH$_3$, +ions) m/e 638 (2M+NH$_4$), 621 (2M+H), 328 (M+NH$_4$), 311 (M+H).

Anal. Calc'd for C$_{11}$H$_{23}$N$_2$O$_4$PS: C, 42.57; H, 7.47; N, 9.03; P, 9.89; S, 10.33 Found: C, 42.95; H, 7.55; N, 9.10; P, 9.81; S, 10.59.

$[\alpha]_D^{20}$=–79° CHCl$_3$, (c=1)

1H NMR (CDCl$_3$, 300 MHz): δ4.35 (q, 2H, J=6.9 Hz) 3.82 (t, 1H, J=14.1 Hz) 3.73 (t, 1H, J=15.0 Hz) 2.93 (td, 1H, J=9.0, 2.0 Hz) 2.80 (td, 1H, J=9.0, 2.0 Hz) 2.67 (d, 3H, J=8.0 Hz) 2.63 (d, 3H, J=8.0 Hz) 2.05 (m, 2H) 1.85 (m, 2H) 1.40 (t, 3H, J=7.0 Hz) 1.30 (m, 4H) ppm.

$^{13}$C NMR (CDCl$_3$, 75.6 MHz): δ67.0 64.3 (d, J=6.8 Hz ) 62.8 (d, J=9.0 Hz) 46.3 (d, J=102.0 Hz ) 28.7 (d, J=2.0 Hz) 27.8 (d, J=10.5 Hz) 27.7 (d, J=8.3 Hz ) 27.4 (d, J=4.5 Hz) 24.0 23.9 ppm.

$^{31}$P NMR (CDCl$_3$, 121.7 MHz): δ26.7 ppm

A(4). [3aR-(3aα,7aβ)]-Octahydro-1,3-dimethyl-1H-1,3,2-benzodiazaphosphole-2-methanesulfonic acid, tetrabutylammonium salt, 2-oxide A suspension of 5.00 g (16.12 mmol) of Part A(3) compound and 6.02 g (16.29 mmol) of tetrabutylammonium iodide in 30 mL of anhydrous THF at RT was stirred for 10 min. at 0° C. and warmed to RT. After 30 h the clear solution was concentrated to a thick oil. The oil was dried under vacuum (0.009 mm Hg) overnight. The honey-like oil was used without further purification.

$^1$H NMR (CD$_3$OD, 300 MHz): δ 3.55 (t, 1H, J=14.1 Hz) 3.50 (t, 1H, J=14.1 Hz) 3.30 (m, 8H) 3.00 (m, 1H) 2.67 (m, 1H) 2.62 (d, 3H, J=10.0 Hz) 2.58 (d, 3H, J=10.0 Hz ) 2.05 (t$_{br}$, 2H, J=10.0 Hz) 1.85 (m, 2H) 1.70 (m, 8H) 1.40 (m, 12H) 1.05 (t, 12H, J=8.0 Hz) ppm.

$^{13}$C NMR (CDCl$_3$, 75.6 MHz ): δ64.1 (d, J=6 Hz ) 63.0 (d, J=6.8 Hz ) 58.6 48.4 (d, J=107 Hz) 29.0 (d, J=2.0 Hz) 28.9 (d, J=4.5 Hz) 27.9 (d, J=10 Hz) 24.2 (d, J=18 Hz) 24.0 23.9 19.6 13.6 ppm.

$^{31}$P NMR (CD$_3$OD, 121.7 MHz): δ35.4 ppm

Mass Spec (FAB, + ions) m/e 242 (Bu$_4$N).

Mass Spec (high res., FAB, – ions)

Calcd for C$_9$H$_{18}$O$_4$N$_2$PS: 281.0725 Found: 281.0717

$[\alpha]_D^{20}$=–33.8° CH$_3$OH, (c=1)

A(5). (S)-(–)-3-Phenoxy-α-phosphonobenzenebutanesufonic acid, tripotassium salt

To a slurry of 3.29 g (6.29 mmol) of Part A(4) compound in 20 mL of dry THF at –90° C. (internal temperature) under argon was added 3.0 mL (7.50 mmol) of 2.5M n-BuLi in hexanes to give a yellow solution. After 0.5 h at –90° C. the solution was treated with 2.10 g (6.29 mmol) of 3-(3-phenoxy-phenyl)propyl iodide in 6 mL of THF at such at rate to keep the internal temperature below –85° C. The reaction mixture was stirred at –90° C. for 3 h after which it was gradually warmed to –74° C. overnight. The mixture was quenched with 360 μL of acetic acid in 3 mL of THF and allowed to warm to RT. The mixture was concentrated and acidified with 12 mL of 2M HCl solution (24 mmol). The reaction mass was extracted with hexane, the aqueous layer was heated to 80° C. for 3 hours and then diluted with 2-propanol until a clear solution resulted. After heating an additional hour the solvent was evaporated and the residue pumped (≈0.5 mm pressure) for 0.5 h. The remainder was dissolved in 30 mL (30 mmol) of 1M KOH solution and freeze dried to provide a cream colored solid. The solid was diluted with water and eluted through 24 g of AG50X8 (63 meq, K$^+$ form) ion exchange resin. Final purification was accomplished by MPLC on a column of CHP20P gel (125 mL) eluting with water (200 mL) followed by a gradient created by the gradual addition of 500 mL of acetonitrile to a reservoir of 500 mL of water. Approximately 10 mL fractions were collected. Pure fractions were pooled, the acetonitrile was removed under reduced pressure and the aqueous solution lyophilized to provide 1.48 g (47%) of title compound as a white lyophilate.

TLC Silica gel (6:3:1 propanol/ammonium hydroxide/water) $R_f$=0.2

Chiral HPLC analysis of enantiomeric excess was performed on a ChromTech α-acid glycoprotein (α1-AGP) column: isocratic 85% 0.1M KH$_2$PO$_4$/15% CH$_3$CN, (pH 4.6) in isocratic mode.

For this sample title compound (S)-isomer: retention time≈10.3 min. 94% ee

Anal. Calc'd for C$_{16}$H$_{16}$O$_7$PSK$_3$+2.2 H$_2$O: C, 35.54; H, 3.81; P, 5.73; S, 5.93 Found: C, 35.54; H, 3.98; P, 5.42; S, 6.30.

A(6). (S)-(–)-3- Phenoxy-α-phosphonobenzenebutanesulfonic acid, 1-adamantanamine(1:2)salt A sample of the (R)-(–)-trisalt (94:6, (S):(R)) prepared in Part A(5) (70 mg, 0.14 mmol) was stirred with 3 g of Ag50-X8 ion exchange resin (7.5 meq, H$^+$form) for 1 h in 5 mL of water and 3 mL of methanol. The mixture was slowly eluted through an additional column of Ag50-X8 ion exchange resin (1 g, 2.5 meq, H$^+$ form) with 1:1 methanol/water. Approximately 3 mL fractions were collected. Fractions #2 to 7 were pooled, the methanol was removed under reduced pressure and the aqueous solution lyophilized to provide 54 mg (100%) of the free acid form of the title salt as a thin film.

The free acid (54 mg, 0.14 mmol) in 3 mL of a 1:1 methanol/water solution was treated with 39 mg (0.28 mmol, 2 eq) of adamantanamine and the mixture stirred for 0.5 h. The mixture was concentrated to a white solid. The solid was recrystallized from hot water and 2-propanol. The white granules were collected to yield 79 mg (85%) of title salt as a 97:3 mixture of (S):(R) enantiomers. The recrystallization procedure was repeated to provide 66 mg (85%) of title salt, as a white solid, mp 248°–252° C. The two recrystallizations from hot 2-propanol/water improved the ratio of (S):(R) enantiomers from 94:6 to 98:2 determined by HPLC as described on the α-acid glycoprotein column.

TLC Silica gel (6:3:1 n-propanol/conc. ammonia/water) $R_f$=0.30.

IR (KBr) 3426, 3086, 3065, 3036, 2915, 2855, 1609, 1582, 1485, 1233, 1215, 1175, 1022, 882 cm$^{-1}$.

$^1$H NMR (CD$_3$OD, 400 MHz ): δ7.30 (t, 2H, J=8.1 Hz ) 7.20 (t, 1H, J=8.0 Hz) 7.07 (t, 1H, J=6.2 Hz ) 6.95 (m, 3H) 6.86 (s, 1H) 6.73 (dd, 1H, J=8.5, 2.5 Hz) 3.05 (dr, 1H, J=18.0, 6.2 Hz) 2.65 (m, 2H) 2.15 (s+m, 8H) 2.00 (m, 2H) 1.90 (s, 12H) 1.75 (d, 6H, J=12.0 Hz) 1.68 (d, 6H, J=12.0 Hz) ppm.

Mass Spec (FAB, + ions) m/e 689 (M+H); (FAB, – ions) m/e 385 (M-2 (C$_9$H$_{17}$N)+H).

Anal. Calc'd for C$_{36}$H$_{53}$O$_7$N$_2$P+1.00 H$_2$O:
C, 61.17; H, 7.84; N, 3.96; P, 4.38; S, 4.54. Found: C, 61.26; H, 7.90; N, 4.00; P, 4.27; S, 4.74.

regeneration of Metal Salt

Title salt (60 mg, 0.08 mmol) was stirred with 1.5 mL of Ag50-X8 ion exchange resin (2.5 meq, K$^+$ form) for 2 h in 3 mL of water and 1 mL of methanol (pH=7). The mixture was slowly eluted through an additional column of Ag50-X8 ion exchange resin (1.5 mL, 2.5 meq, K$^+$ form) with 1:1 methanol/water. Product containing fractions were pooled, the methanol was removed under reduced pressure and the aqueous solution lyophilized to provide 38 mg (95 %) of the tripotassium salt as a white lyophilate.

Chiral HPLC analysis of enantiomeric excess was performed on a ChromTech Q-acid glycoprotein (α1-AGP) column eluted with isocratic 85% 0.1M $KH_2PO_4$, 15% $CH_3CN$, pH 4.6.

For this sample, title (S)-isomer: retention time≈9.5 min. 98% ee

B. (S)-α-[Bis[[[(2,2-dimethylpropoxy)carbonyl]oxy]methoxy]phosphinyl]-3-phenoxybenzenebutanesulfonic acid potassium salt To a solution of Part A compound (110 mg, 0.29 mmol) and Example 2 Part B iodide (235 mg, 0.86 mmol) in 1.4 mL of dry acetonitrile was added diisopropylethyl amine (DIPEA) (126 μl, 0.75 mmol) slowly at room temperature over an hour and the mixture was stirred for 1 day. The reaction mixture was diluted with 10 mL EtOAc and was washed with 10 mL of pH 2 phosphate buffer, 10 mL of pH 6 phosphate buffer, brine, and dried over $Na_2SO_4$. The filtrate was then concentrated in vacuo and isolated by Prep HPLC using 53% B (as specified in the analytical HPLC conditions below) as a mobile phase to give the desired product, as an ammonium salt in 44% yield. The final product was combined with two previous batches which were prepared by the same conditions and washed with pH 2 phosphate buffer (2×10 mL), pH 6 phosphate buffer (2×10 mL), saturated KCl, dried over anhydrous KCl. The filtrate was concentrated in vacuo to give the title compound with enantiomeric purity 98.3%.

M.S.: TCW 625 (M-H)⁻ at 673⁻

$[\alpha]^D$: −16.67° [MeOH, c; 0.18]

$^1$H NMR: (400 MHz/CDCl$_3$): 7.35–6.69 (m's, 9H), 5.58–5.81 (m, 4H), 3.75–3.90 (m, 4H,), 3.60–3.41 (m, 1H), 2.62–2.52 (m, 2H), 2.25–1.75 (m, 4H), 0.89 (m, 18H).

$^{13}$C NMR: (100 MHz/CDCl$_3$): 157.4, 157.0, 154.2, 154.1, 144.1, 129.6, 129.4, 123.4, 122.9, 119.1, 118.7, 116.0, 85.0, 78.1, 35.3, 31.3, 29.6, 26.1

HPLC: Rt=15.31 minutes (99%, UV 215); EM Lichrosphere select B (c-8, 5μ, 4×250 70%; A: 95% $H_2O$/5% $CH_3CN$+0.01M $NH_4OAc$, pH 5.5; solvent B: 95% $CH_3CN$/ 5% $H_2O$+0.01M $NH_4OAc$, pH 5.5

Elemental Analysis for $C_{30}H_{42}O_{13}SP.K.0.14\ H_2O$: Calculated: C 50.37; H 5.96; P 4.33; S 4.48 Found: C 50.37; H 5.91; P 4.17; S 4.88

EXAMPLE 2

α-[Bis[[[(2,2-dimethylpropoxy)carbonyl]oxy]methoxy] phosphinyl]-3-phenoxybenzenebutanesulfonic acid, potassium salt.

A.

Chloromethyl chloroformate (3.2 mL, 40 mmol ) was added slowly to a stirred solution of 3.2 mL (40 mmol) of dry pyridine and 3.53 g (40 mmol) of neopentyl alcohol in 50 mL of dry $CH_2Cl_2$ under argon (internal temperature less than −20°). The cooling bath was removed and the reaction was stirred at room temperature for 16 hours. The reaction was diluted with $CH_2Cl_2$ and the $CH_2Cl_2$ was washed with water (4×), dried ($Na_2SO_4$), and concentrated to an oil. Distillation of the oil at 12 mm gave 5.77 g (80% yield) of title compound with bp 80°/12 mm.

B.

A mixture of Part A compound (2.71 g, 15 mmol) and anhydrous NaI (10.0 g, 66.7 mmol) in 100 mL of dry $CH_3CN$ was stirred at 65° for 2 hours. The reaction was concentrated to a residue, which was taken up in $Et_2O$ and water. The ether layer was washed with water (2×), dilute aqueous thiosulfate, water (2×), dried (magnesium sulfate) and concentrated to give 4.18 g (ca. quantitative yield) of title compound as a colorless oil.

C.

3-Phenoxy -α-phosphonobenzenebutanesulfonic acid

C(1) Reaction of neopentyl alcohol with methanesulfonyl chloride

To a solution of 200 grams (2.27 mol) of neopentyl alcohol in 1.5 liters of methylene chloride was added 348 mL (2.497 mol) of triethylamine. The solution was cooled to −5° C. (ice-methanol bath) and methanesulfonyl chloride (185 ml, 2,39 mol) was added dropwise over 35 minutes maintaining the reaction temperature below 17° C. The reaction was stirred for 1.5 hours maintaining the reaction temperature at −3° C. To the reaction mixture 1000 mL of water was added and the mixture placed in a separatory funnel for extraction. The pH of the aqueous layer was 4.4. The separated organic phase was further washed with 500 mL of 1N HCl, 500 mL of saturated sodium bicarbonate and 500 L of saturated brine. The methylene chloride solution was dried over magnesium sulfate and concentrated in vacuo to afford 397.78 grams of an oil 105.5% yield. The orange oil was distilled bp 80°–83° C. 0.05 mm to afford 370 grams (98.1% yield) of the mesylate.

C(2) Reaction of the above mesylate with diethyl chlorophosphate to make the neopentyl sulfonate To 370 grams (2.26 mol) of the Part C(1) mesylate in 1000 mL sure seal THF was added 900 mL of a 2.5M butyl lithium solution in hexane dropwise over 40 minutes at −75° C.—60° C. The cooling bath was removed and the solution allowed to warm to −30° C. over 30 minutes. The solution was cooled back down to −78° C. and diethyl chlorophosphate (165 mL; 1.14 mol) was added dropwise over 20 minutes maintaining the reaction temperature below −60° C. The reaction was stirred at −78° C. for two hours. The reaction was then quenched with 130 mL of acetic acid. The THF was removed in vacuo and the resulting oil was dissolved in methylene chloride. The methylene chloride solution was washed with water followed by two saturated sodium bicarbonate washes. The organic extract was dried over magnesium sulfate and Darco© to afford 474.9 grams of a red oil. The residual neopentyl mesyl starting material was removed by distillation boiling point 65° C. oil bath 95° C., 0.05 mm. It should be noted that decomposition of the desired product took place when the bath temperature was 165° C. The neopentyl sulfonate was obtained and used without further purification.

C(3) Coupling of the iodo unit with the neopentyl sulfonate

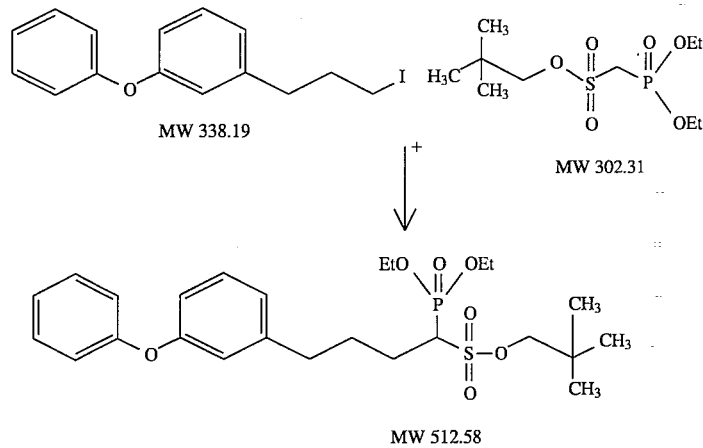

To 8.19 grams (204.77) of sodium hydride 30 mls of hexane was added. The mixture was stirred and allowed to settle. Hexane was decanted away from the sodium hydride. This was repeated two more times. To the sodium hydride 280 mL DMF was added and the mixture cooled down to 0° C. using an ice bath. The Part C(2) neopentyl sulfonate was dissolved in 110 mL of DMF and added over 20 minutes maintaining the temperature at 0° C. The reaction was warmed to room temperature and stirred for 30 minutes. The mixture was cooled back down to 0° C. The iodo-compound (43.01 g, 127.18 mmol) dissolved in 200 mL DMF was added over 20 minutes to the above mixture maintaining the reaction temperature at 0° C. The reaction was stirred for two hours at 0° C. The reaction mixture was allowed to warm to room temperature and stirred overnight. The reaction was checked by HPLC; the product has a retention time of 7.9 minutes. One also observes starting iodo- compound, retention time=11.104 minutes, 0.33%, and dialkylated material, retention time=31.893 minutes, 1.6%. The reaction was quenched with 500 mL of water. The aqueous mixture was extracted with 3 1.5 liters of methyl tert butyl ether. The organic solution was washed with 300 mL of brine and dried over magnesium sulfate. The dried solution was filtered and stripped to afford 117.22 grams of an oil, (theoretical yield 65.2 grams). This material was purified by chromatography using silica gel. The mixture was eluted initially with a 5% ethyl acetate/hexane mixture and gradually increasing to a 45% ethyl acetate hexane mixture. The fractions were analyzed and combined. The cut containing the rich mono-alkylated material was collected and the cuts that contained both the dialkylated and mono-alkylated material were combined. The latter cuts were passed through a C-18 pad to removed the dialkylated material using a 70:30 acetonitrile::water mixture. The cuts that contained the clean mono-alkylated material were concentrated in vacuo to remove acetonitrile and then the aqueous layer was extracted with methylene chloride. The mono-alkylated material from the C-18 pad purification and the mono-alkylated material were combined to afford 55.34 grams, 84.9% yield pure mono-alkylated material.

C(4) Hydrolysis of the tri-ester to the tri-acid 20 grams of the Part C(3) tri-ester was treated with 300 mls of 6N HCl. The mixture was heated to reflux. The reaction was monitored by HPLC product 6.38 minutes. The starting tri-ester 27.72 minutes. The above mixture over night became homogenous. The solution was refluxed until the reaction was judged complete by HPLC after 3–5 days. The reaction appears complete when the AP (apparent purity) of the desired product is somewhere between 91–93. The reaction solution was stripped to an oil. Toluene and acetonitrile was added to remove residual water as needed. The oil was then passed through a pad of C-18 YMC BAQ 500S 550 ODS AQ using a 70:30 water acetonitrile mixture. The cuts were monitored using HPLC method 15 triacid peak 2.7 minutes. The major impurity at 26 minutes is held up on the C18. The desired cuts were combined and stripped to afford 14.335 grams of title tri-acid, 81% yield, AP 98.9%.

D. α-[Bis[[[(2,2-dimethylpropoxy)carbonyl]oxy]methoxy]phosphinyl]-3-phenoxybenzenebutanesulfonic acid, potassium salt To a stirred solution of Part C compound (417 mg, 1.08 mol, dried by concentration with EtoAc/toluene) in dry acetonitrile (3 mL) under argon was added Hunig's base (580 μl, 3.35 mmol). The mixture was stirred at room temperature for 5 minutes and then treated with Part B compound (882 mg, 3.24 mmol) in acetonitrile (1 mL). The clear reaction mixture was heated with stirring to 45° C. The reaction mixture was concentrated in vacuo to give a white residue. The residue was taken up into ethyl acetate (100 mL) and washed with 5% aqueous $KH_2PO_4$ buffer (pH=2, 3×30 mL). The aqueous layer was extracted with ethyl acetate (2×25 mL). The combined ethyl acetate extract was washed with 5% aqueous $KH_2PO_4$ buffer (pH=6, 2×30 mL), brine (30 mL), dried over anhy. KCl and concentrated in vacuo to give 840 mg of orange oil. The oil was purified by HP-20 chromatography (130 mL of HP-20, 20–50% $CH_3CN/H_2O$ step gradient) using 7 psi pressure to give after lyophilization (310 mg, 40.3%) of the title compound as a white foam.

MS: $(M+K)^+713^+$

Analysis: For $C_{30}H_{42}O_{13}PS.K$ Calculated: C, 50.55; H, 5.94; S. 4.50; P, 4.35 Found: C, 50.50; H, 5.97; S, 4.67; P, 4.03

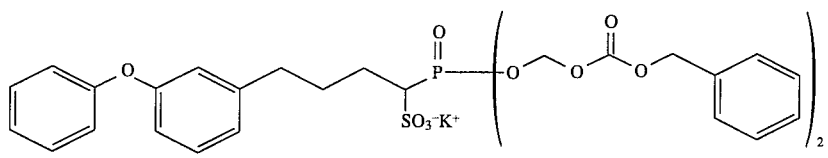

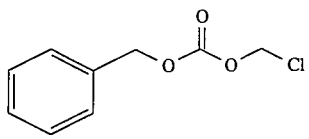

To a solution of 2.41 mL (23.27 mmol) of benzyl alcohol and 1.88 mL (23.27 mmol) of pyridine in 15 mL of $CH_2Cl_2$, cooled to −78° C., was added dropwise a solution of 3.00 g (23.27 mmol) of chloromethyl chloroformate in 5 mL of $CH_2Cl_2$. After 10 minutes, the reaction was warmed to room temperature and stirred for 16 hours. The crude reaction mixture was diluted with 40 mL $CH_2Cl_2$ and washed with 2–30 mL portions of brine, dried (magnesium sulfate) and concentrated in vacuo to give a clear liquid. The crude liquid was distilled (90–94° C., 0.1 mm Hg) to give 3.53 g (17.60 mmol, 76%) of title carbonate as a clear liquid.

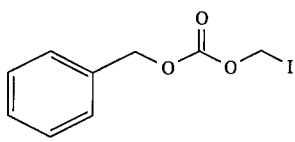

To a solution of 2.52 g (12.58 mmol) of Part A chloride in 15 mL of $CH_3CN$ was added 7.54 g (50.32 mmol) of sodium iodide in one portion. The reaction was heated to 50° C. and stirred for 2 hours, then filtered. The resulting filtrate was concentrated in vacuo to give an orange solid. The solid was rinsed with 3–75 mL portions of ether to extract the product from the salts; the combined ether layers were dried (magnesium sulfate) and concentrated in vacuo to give 3.36 g (11.50 mmol, 91%) of title iodide as a red oil.

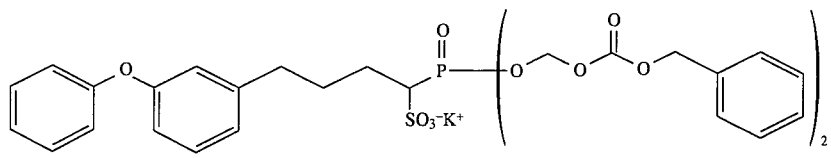

A portion of 300 mg (0.77 mmol) of Example 2 Part C triacid was azeotroped three times with EtoAc/toluene and dried in vacuo to give a clear reddish oil. To a solution of the triacid in 10 mL acetonitrile was added dropwise 420 μl (4.00 mmol) of Hunig's base, followed by the dropwise addition of 1.40 g (4.81 mmol), of Part B iodide in 2 mL of acetonitrile. The reaction was stirred at 45° C. for 5 hours, then diluted with 50 mL of EtoAc and washed with 2–30 mL portions of 5% pH 2 $KH_2PO_4$ buffer, 2–30 mL portions of 5% pH 6 $KH_2PO_4$ buffer, 1–30 mL portion of saturated KCl solution, dried (anhydrous KCl) and concentrated in vacuo to give 1.64 g of a crude solid. The crude solid was purified by HP-20 chromatography (120 mL of HP-20, 20–60% $CH_3CN/H_2O$ step gradient; product eluted at 35%) to give 345 mg (0.46 mmol, 59%) of title diester as a white foam.

IR (KBr): 3437, 1765, 1584, 1487, 1456, 1273 $cm^{-1}$.

MS (CI): $753^+$ $(^+H)^+$.

HPLC: $R_T$=21.16 minutes (100% total area, UV 215 nM); EM Lichrosphere select B (C-8, 5μ) 4×250 mm; 28–70% over 23 minutes, 1 mL/min ($CH_3CN+5\%$ $H_2O/0.04M$ $NH_4OAc+5\%$ $CH_3CN$, pH 5.5).

Analysis Calculated for $C_{34}H_{34}KSPO_{13}.0.51$ mol $H_2O$: Calculated: C, 53.60; H, 4.63; P, 4.07; S, 4.21 Found: C, 53.37; H, 4.46; P, 4.08; S, 4.34

EXAMPLE 4

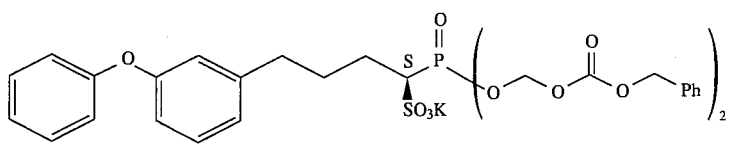

(contains 90% of S-isomer and 10% of R-isomer)

(S)-α-[Bis[[[(phenylmethoxy)carbonyl]oxy]methoxy]phosphinyl]-3-phenoxybenzenebutanesulfonic acid, potassium salt The Example 1 Part A chiral triacid was azeotroped with EtoAc/toluene (3×) and dried in vacuo overnight to give a clear brown oily film (234 mg).

To a solution of the above oily film of the Example 1 Part A chiral triacid (234 mg, 0.6056 mmol) in $CH_3CN$ (Aldrich Sure Seal, 2 mL) at room temperature was added dropwise a solution of Example 3 Part B iodide in 1 mL $CH_3CN$ (Aldrich Sure Seal). The resultant light brown solution was warmed up to 45° C. (oil bath) under argon. To the above stirring solution was added very slowly diisopropylethylamine (Fluka, 295 μL, 1.6958 mmol, 2.8 eq) over 1 hour. After addition of diisopropylethylamine, the reaction mixture was stirred at 45° C. for an additional 6 hours (the progress of the reaction was monitored by analytical HPLC at 3 hours, 4.5 hours and 6 hours, respectively; no change on the formation of the product between 4.5 hours and 6 hours was observed). The reaction mixture was allowed to cool down to room temperature and was stored in a −80° C. freezer overnight.

The reaction mixture (frozen) was allowed to warm up to room temperature and diluted with EtoAc (80 mL), washed with 5% potassium phosphate monobasic pH 2 (3×10 mL), 5% potassium phosphate monobasic pH 6 (2×10 mL), brine (2×20 mL), dried over $Na_2SO_4$, filtered, concentrated, and dried in vacuo to yield 0.61 g crude product as a brownish oil. The crude product was purified (preparative HPLC (three injections, using 2 EM Merck, RP Select B columns and eluting with 48% isocratic B:A (B=95% $CH_3CN/H_2O$; A=95% $H_2O/5\%$ $CH_3CN+0.4M$ $NH_4OAc$, pH 5.5) at a rate of 35 mL/minute, detecting at 215 nm). The desired fractions were combined and lyophilized to give 250 mg of desired product as an ammonium salt form.

The ammonium salt was dissolved in 100 mL of EtoAc, washed with 5% potassium phosphate monobasic pH 2 (1×10 mL), 5% potassium phosphate monobasic pH 6 (2×10 mL), saturated KCl solution (1 ×10 mL), dried over KCl, filtered and concentrated. The residue was dissolved in $CH_3CN/H_2O$, frozen and lyophilized to give the title compound as a potassium salt form (252 mg, 55.3%).

Mass Spec.: (FAB); (M−K)⁻ at 713, MW=752.

IR: (KBr pellet) 3437, 1765, 1584, 1487, 1456, 1406, 1273, 1246, 1219, 1159, 1065, 1030, 1005, 947, 89, 694 cm⁻¹.

¹H-NMR: 270 MHz; $CD_3OD$ (+ drops of $CDCl_3$): δ1.86 (m, 2H), 1.93, 2.10 (m's, 2H), 2.54 (t, 2H, J=7.7 Hz), 3.36, 3.42 (dt, 1H, J=5.5, 20 Hz), 5.14 (d, 4H, J=2.5 Hz), 5.66 (m, 4H), 6.74 (d, 1H, J=7.0 Hz), 6.83 (s, 1H), 6.95 (m, 3H), 7.05 (t, 1H, J=7.4 Hz), 7.20 (t, 1H, J=7.7 Hz), 7.32 (m, 12H).

¹³C-NMR: 100 MHz; $CD_3OD$: δ158.5, 158.3, 155.0, 54.9, 145.1, 135.9, 130.6, 130.4, 129.5, 129.4, 129.3, 124.4, 123.9, 119.9, 119.5, 119.1, 86.2, 85.8, 1.2, 60.8, 58.7, 54.5, 36.2, 30.6, 28.0.

Analysis Calculated for $C_{34}H_{34}O_{13}SPK$; Calculated: C, 54.26; H, 4.55; P, 4.12; S, 4.26; Found: C, 53.99; H, 4.26; P, 4.01; S, 4.40.

HPLC: Rt=14.15 minutes (98.7%, UV 215); EM Lichrosphere select B (C-8, 5μ, 4×250 mm) 28–70% B:A (B=95% $CH_3CN/5\%$ $H_2O+0.01M$ $NH_4OAc$, pH 5.5; A=95% $H_2O/5\%$ $CH_3CN+0.01M$ $NH_4OAc$, pH 5.5), 1 mL/minute.

EXAMPLE 5

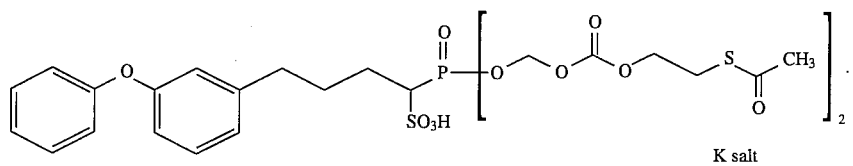

K salt

α-[Bis[[[[2-(acetylthio)ethoxy]carbonyl]oxy]methoxy]phosphinyl]-3-phenoxybenzenebutanesulfonic acid, potassium salt

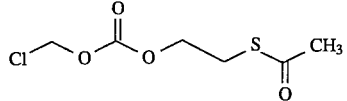

To a suspension of NaH (6.00 g of a 60% suspension in oil; prewashed with dry THF [2×30 mL]) in THF (120 mL) was added dropwise a solution of thiolacetic acid (11.48 g; 0.150 mol) in THF (20 mL). The suspension was stirred at 0° C. for 1 hour under argon. A solution of 2-bromoethanol (10.63 mL; 0.150 mol) in THF was then added dropwise over 30 minutes. The reaction was allowed to warm to room temperature and stirred for 18 hours. The mixture was added to EtoAc and $H_2O$ (100 mL each). The aqueous layer was extracted with EtoAc (3×75 mL). The combined organic extracts were dried ($Na_2SO_4$) and concentrated in vacuo to afford a yellow oil. This was distilled (b.p.=86°–100° C. at 20 mm Hg) to give the title thiolester (14.32 g; 79%) as a yellow liquid.

¹H NMR ($CDCl_3$): δ2.11 (m, 1H), 2.37 (s, 3H), 3.09 (t, 2H, J=6.1 Hz), 3.77 (q, 2H, J=5.9 Hz)

¹³C NMR ($CDCl_3$): δ30.5, 31.8, 61.3, 196.3

To a 0° C. solution of Part A thiolester alcohol (4.00 g; 33.3 mmol) and dry pyridine (2.70 mL; 33.3 mmol) in CH$_2$Cl$_2$ (30 mL) under argon was added dropwise chloromethyl chloroformate (2.96 mL; 33.3 mmol) over 10 minutes. The mixture was stirred at 0° C. for 1 hour and then at room temperature for 12 hours. CH$_2$Cl$_2$ and H$_2$O (50 mL each) were added. The organic phase was washed with H$_2$O (3×30 mL), dried (magnesium sulfate) and concentrated in vacuo to afford a yellow oil. This was distilled (b.p=82°–85° C. at 1.5 mm Hg) to furnish the title α-chloro carbonate (5.99 g; 85%) as a yellow oil.

$^1$H NMR (CDCl$_3$): δ2.37 (s, 3H), 3.19 (t, 2H, J=6.4 Hz), 4.32 (t, 2 H, J=6.4 Hz), 5.74 (s, 2H)

$^{13}$C NMR (CDCl$_3$): δ27.4, 30.3, 66.9, 72.2, 152.9, 194.4

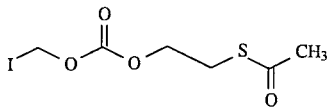

A mixture of the Part B α-chloro carbonate (4.00 g; 18.8 mmol) and NaI (14.09 g; 94.0 mmol) in anhydrous MeCN (150 mL) was heated in a 65° C. oil bath under argon for 3 hours. The reaction mixture was allowed to cool to room temperature and concentrated in vacuo. The residue was partitioned between H$_2$O and Et$_2$O (150 mL each). The aqueous layer was extracted with Et$_2$O (2×50 mL). The combined organic extracts were washed with H$_2$O (3×50 mL), 10% aqueous sodium thiosulfate (2×50 mL), H$_2$O (2×50 mL), brine (2×50 mL) and dried (magnesium sulfate). Solvents were removed in vacuo to give the crude title α-iodo carbonate (5.77 g; >100%) as a yellow oil, which was used in the next step without further purification.

$^1$H NMR (CDCl$_3$): δ2.37 (s, 3H), 3.18 (t, 2H, J=6.4 Hz), 4.32 (t, 2H, J=6.4 Hz), 5.96 (s, 2H)

$^{13}$C NMR (CDCl$_3$): δ27.4, 30.4, 33.9, 66.7, 152.6, 194.3

D. α-[Bis[[[[2-(acetylthio)ethoxy]carbonyl]oxy]methoxy]phosphinyl]-3-phenoxybenzenebutanesulfonic acid, potassium salt The Example 2 Part C racemic triacid was azeotroped with EtOAc/toluene (3×20 mL) and dried in vacuo to give a clear yellow oily film (430 mg). To a 0° C. solution of the yellow oily film (430 mg, 1.11 mmol) in CH$_3$CN (3 mL) was added dry iPr$_2$NEt (0.638 mL; 3.66 mmol) and the solution was stirred at 0° C. for 15 minutes. A solution of Part C iodide (1.046 g; 3.44 mmol) in dry MeCN (2.0 mL) was added dropwise and the resultant yellow solution was stirred under argon at room temperature (the flask was wrapped in aluminum foil to protect the reaction from light) for 72 hours. The reaction solution was then concentrated in vacuo. The residue was partitioned between EtOAc (50 mL) and pH 2 buffer (5% aqueous KH$_2$PO$_4$; 25 mL). The organic phase was successively washed with additional pH 2 buffer (5% aqueous KH$_2$PO$_4$; 2×25 mL), pH 6 buffer (5% aqueous KH$_2$PO$_4$; 2×25 mL), brine (2×25 mL), dried (Na$_2$SO$_4$) and finally concentrated in vacuo to afford the crude product as a beige foam. This was purified by preparative HPLC [five injections, using 2 EM Merck, RP Select B columns and eluting with 40% isocratic B:A (B=95:5 CH$_3$CN:H$_2$O ; A=95:5 H$_2$O:CH$_3$CN+0.04M aqueous NH$_4$OAc, pH 5.5) at a flow rate of 35 mL/minute, UV detection at 215 nm]. The desired fractions were combined and concentrated in vacuo to a minimal volume (20 mL), then lyophilized to give the desired product as its ammonium salt (a gummy solid). This residue was dissolved in EtOAc (75 mL) and washed with pH 2 buffer (5% aqueous KH$_2$PO$_4$; 2×25 mL), pH 6 buffer (5% aqueous KH$_2$PO$_4$; 2×25 mL), saturated aqueous KCl (1×10 mL), dried (anhydrous KCl), and finally concentrated in vacuo. The oily yellow residue was lyophilized from MeCN/H$_2$O to afford the title compound (0.375 g, 43%) as a white lyophilate.

m.p.=67°–71° C.

MS: (Electrospray); (M+NH$_4$)$^+$=756, MW=738 (free acid)

IR (KBr disk): cm$^{-1}$ 3435, 1765, 1696, 1584, 1487, 1248, 1217, 1136, 1030, 949, 789, 627.

$^1$H-NMR (300 MHz; CD$_3$OD): δ1.78–2.03 (m, 2H), 2.06–2.39 (m, 2H), 2.30 (s, 6H), 2.51–2.61 (m, 2H), 3.08–3.13 (m, 4H), 3.52 (m, 1H), 4.18–4.24 (m, 4H), 5.57–5.82 (m, 4H), 6.72–7.32 (m, 9H).

$^{13}$C-NMR (70 MHz; CD$_3$OD): δ27.2, 27.4, 29.5 (d, J=5.8 Hz), 30.5, 35.3, 58.6 (d, J=137 Hz), 66.9, 85.2, 116.1, 118.7, 119.1, 123.0, 123.4, 129.5, 129.7, 144.2, 153.6, 157.0, 157.3, 194.8

Elemental Analysis: (for C$_{28}$H$_{34}$O$_{15}$PS$_3$K) Calculated: C, 43.29; H, 4.41; P, 3.99; S, 12.38; Found: C, 43.05, H, 4.42; P, 3.55, S, 12.06

HPLC: Retention time=14.5 minutes (100% purity, UV detection at 215 nm); EM Lichrosphere select B (C-8, 5μ, 4×250 mm). Method: continuous gradient over 20 minutes: 28–72% B:A (B=95% CH$_3$CN:H$_2$O+0.10M NH$_4$OAc, pH 5.5; A=95% H$_2$O : CH$_3$CN+0.01M NH$_4$OAc, pH 5.5) flow rate =1 ml/minute.

What is claimed is:

1. A prodrug ester of a phosphonosulfonate salt having the structure

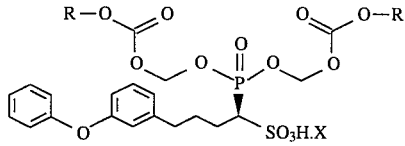

wherein R is acylthioalkyl and X represents a pharmaceutically acceptable salt, including all stereoisomers thereof.

2. The prodrug ester as defined in claim 1 wherein R is alkanoylthioalkyl.

3. The compound as defined in claim 1 which is

α-[bis[[[2-(acetylthio)ethoxy]carbonyl]oxy]methoxy] phosphinyl]-3-phenoxybenzenebutanesulfonic acid; or a pharmaceutically acceptable salt thereof.

4. A prodrug ester of a phosphonosulfonate salt having the structure

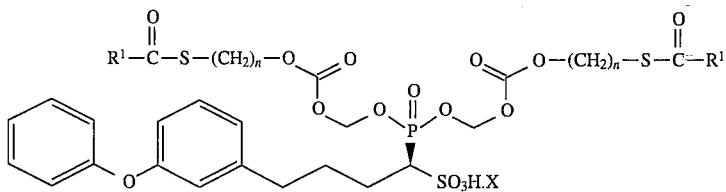

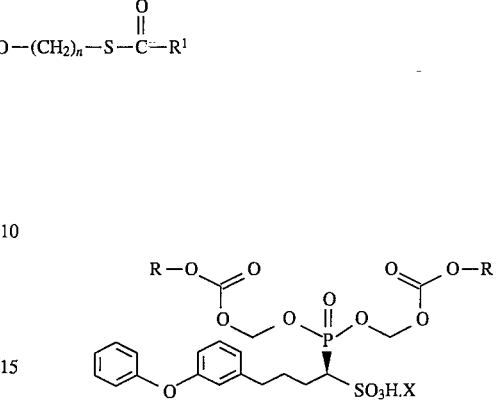

wherein $R^1$ is alkyl, arylalkyl or aryl, n is 2 to 6, and X represents a pharmaceutically acceptable salt, including all stereoisomers thereof.

5. The prodrug ester as defined in claim 4 wherein $R^1$ is alkyl.

6. The prodrug ester as defined in claim 4 wherein

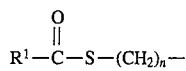

is

7. A pharmaceutical composition comprising a phosphonosulfonate salt as defined in claim 1 and a pharmaceutically acceptable carrier therefor.

8. A method of inhibiting cholesterol biosynthesis, lowering serum cholesterol, or inhibiting or treating hyperlipemia, hyperlipidemia, hyperlipoproteinemia, hypercholesterolemia, or hypertriglyceridemia, or inhibiting or treating atherosclerosis, which comprises administering to a patient in need of such treatment a therapeutically effective amount of a compound having the structure wherein R is acylthioalkyl and X represents a pharmaceutically acceptable salt, including all stereoisomers thereof.

9. The method as defined in claim 8 wherein R is alkanoylthioalkyl.

10. The method as defined in claim 8 wherein the R is

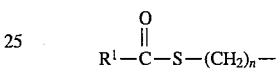

wherein $R^1$ is alkyl, aryl or arylalkyl and n is an integer from 2 to 6.

11. The method as defined in claim 8 for treating atherosclerosis.

12. The method as defined in claim 8 for treating hypercholesterolemia.

* * * * *